United States Patent [19]

Argyropoulos et al.

[11] Patent Number: 4,970,334
[45] Date of Patent: Nov. 13, 1990

[54] PROCESS FOR PREPARING ESTERS OF UNSATURATED ALCOHOLS

[75] Inventors: John N. Argyropoulos, Dunbar; Brian T. Keen, Charleston, both of W. Va.

[73] Assignee: Union Carbide Chemicals and Plastics Company Inc., Danbury, Conn.

[21] Appl. No.: 91,196

[22] Filed: Aug. 31, 1987

[51] Int. Cl.$^5$ .............................................. C07C 67/02
[52] U.S. Cl. .................................................. 560/261
[58] Field of Search ................... 560/261, 231, 254, 1, 560/113, 122, 105; 260/405.5

[56] References Cited

U.S. PATENT DOCUMENTS 3,408,388  10/1968  Hagemeyer et al. ............... 560/262

FOREIGN PATENT DOCUMENTS 1288423  9/1972  United Kingdom.
1288615  9/1972  United Kingdom.
1290094  9/1972  United Kingdom.

Primary Examiner—Werren B. Lone
Attorney, Agent, or Firm—Reynold J. Finnegan

[57] ABSTRACT

A process for the catalytic dehydration of saturated 2,2,4-trisubstituted glycol monoesters at elevated temperatures to unsaturated 2,2,4-trisubstituted monoesters in the presence of a non-volatile acid catalyst.

14 Claims, No Drawings

PROCESS FOR PREPARING ESTERS OF UNSATURATED ALCOHOLS

FIELD OF THE INVENTION

This invention relates to a process for preparing esters from saturated alcohols. More specifically it pertains to a continuous process for preparing esters of unsaturated alcohols by the catalytic dehydration of 2,2,4-trisubstituted glycol monoesters.

DESCRIPTION OF THE PRIOR ART

The process for producing esters of unsaturated alcohols from monoesters of saturated 2,2,4 trisubstituted-1,3-diols has long been known and was patented by Hagemeyer et al. in U.S. Pat. No. 3,408,388 on Oct. 29, 1968. The process disclosed in this patent involves contacting a glycol monoester with a highly acidic, nonvolatile catalyst at a temperature in the range of from about 90° C. to about 160° C. to cause dehydration and formation of the corresponding ester of an unsaturated 2,2,4-trisubstituted alcohol. The acidic catalysts useful are discussed in column 3, lines 20–25, column 4, line 73 to column 5, line 13 and in claim 1 at column 11, lines 1 to 5 of U.S. 3,408,388. In this discussion, the patentees, at column 5, lines 8 to 13, specifically state, concerning the suitable catalysts, that "The members of the group of specific dehydration catalysts are somewhat exclusive in effect inasmuch as other nonvolatile compounds such as potassium acid sulfate—are not effective under the conditions of this invention." Thus, the patentees have taken the positive position, apparently based on their experiences with their process, that potassium acid sulfate is not a catalyst for the dehydration of the defined saturated glycol monoesters to the corresponding esters of unsaturated 2,2,4-trisubstituted alcohols. In addition, this patent reference also teaches that the dehydration should be carried out at a temperature range substantially from 90° C. to 160° C. with the optimum range being substantially from 110° C. to 135° C. and presents a detailed discussion of the disadvantages of operating outside the defined broad range. It states that at "a dehydration temperature above 160° C., the dehydration of the glycol monoester is nearly complete but the principal products of the reaction include the ester of the unsaturated alcohol, the acid, substituted tetrahydrofurans and other products which are formed by an initial cracking or rearrangement reaction". The patentees are clearly advising the industry that a temperature above 160° C. is to be avoided and unsatisfactory and leads to considerable undesired quantities of many by-products. The teachings in U.S. Pat. No. 3,408,388 are completely contrary to what was found by the inventors of this instant patent application, both as to temperature and products, as will be seen below. The patentees' discussion in U.S. Pat. No. 3,408,388 on temperature is found at column 5, lines 29 to 46.

British Patent Specification No. 1,288,615, published Sept. 13, 1972, issued to Bertram Yeomans and assigned to BP Chemicals Ltd., relates to the production of 2,2,4-trimethylpentanol-1. In the process one step involves the dehydration of 3-hydroxy-2,2,4-trimethylpentyl-1 isobutyrate to 2,2,4-trimethylpentenyl isobutyrate. This dehydration is carried out by heating the saturated ester in contact with an acid catalyst, at 90° C. to 300° C., together with an entrainer for the azeotropic removal of water for a period of 5 to 50 hours, preferably 12 to 36 hours (page 2, lines 13 to 37). Example 1 (page 2, lines 87 to 100) and Example 2 illustrate this azeotropic procedure. Though product is obtained the selectivity to 2,2,4-trimethylpentenyl isobutyrate is relatively low; in Example 1 it is about 83% and Example 2 shows values of 62% and 57% for two of the three experiments. These selectivities are considerably lower than those obtained by the instant applicants. Further, applicants' process does not require the entrainer and the average contact time in the reaction is less.

British Patent Specification No. 1,290,094, published Sept. 20, 1972, issued to Bertram Yeomans and assigned to BP Chemicals Ltd., relates to the transesterification of 2,2,4-trimethylpentane- 1,3-diol with 2,2,4-trimethylpentyl-1 isobutyrate in the presence of a metal, alkoxide, oxide or hydroxide of a metal of a main group element of Group I or Group II of the Periodic Table to produce 2,2,4-trimethylpentanol-1. In the description of the process an intermediate dehydration step is disclosed (page2, lines 29 to 87) for dehydrating hydroxy-2,2,4-trimethylpentyl-1 isobutyrate in admixture with added 2,2,4-trimethylpentyl-1,3- diisobutyrate (with the dibutyrate ester content in the reaction preferably being greater than 30 weight percent) to the unsaturated 2,2,4-trimethylpentenyl-1 isobutyrate. This is stated as being accomplished using an acid catalyst at 120° C. to 200° C. over a reaction time of from 20 to 60 hours preferably 30 hours (page 2, lines 82–83). The reference requires deliberate addition of the diester (page 2, lines 53–54 and lines 63–78).

SUMMARY OF THE INVENTION

A process for the production of unsaturated 2,2,4-trisubstituted monoesters by the catalytic dehydration of a saturated 2,2,4-trisubstituted glycol monoester in contact with a catalytic amount of non-volatile acid catalyst at a reactor temperature of from about 170° C. to about 270° C.

DESCRIPTION OF THE INVENTION

This invention provides a continuous process for dehydrating saturated 2,2,4-trisubstituted glycol monoesters of general formula I, hereinafter shown, to unsaturated 2,2,4-trisubstituted monoesters of general formulas II and III, hereinafter shown, in high yield rate and conversion at yields approaching 95 percent under conditions that were not heretofore considered capable of producing the unsaturated monoesters. In the process of this invention it was found that temperatures and catalysts heretofore considered unsuitable for the dehydration of the saturated 2,2,4 trisubstituted glycol monoesters to their corresponding unsaturated 2,2,4-trisubstituted monoesters can be used in a continuous process to obtain the desired unsaturated product in high yield. The present invention does not require deliberate addition of entrainer or diester.

In the condensation of aldehydes to their corresponding saturated 2,2,4-trisubstituted glycol monoesters, the product obtained is generally a mixture of two isomers having the formulas IV and V:

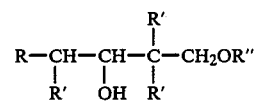

-continued

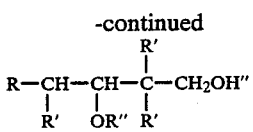   V

This condensation reaction is well known and fully documented in U.S. Pat. No. 3,091,632 (Hagemeyer et al., May 28, 1963), U.S. Pat. No. 3,291,821 (Perry et al., Dec. 13, 1966) and U.S. Pat. No. 3,718,689 (McCain et al., Feb. 27, 1973) all of which describe various catalytic methods for their production and uses for these compounds.

An important use for these saturated compounds is as the starting materials for the unsaturated 2,2,4-trisubstituted monoesters, which are obtained by an acid catalyzed dehydration reaction. The dehydration of isomeric mixtures of IV and V yields a mixture of unsaturated 2,2,4-trisubstituted monoesters of formulas II and III:

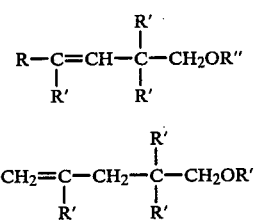

However, unless care is taken in conducting the reaction, considerable losses can be sustained by formation of unwanted by-products. For example, disproportionation of compounds IV and V can result in the formation of the diester:

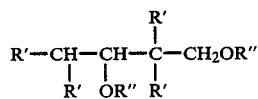

in which both R″ groups are —OCR′ groups and the diol:

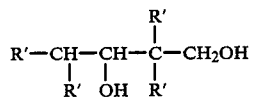

Though the diester is relatively stable, the diol dehydrates rapidly to the unsaturated alcohols:

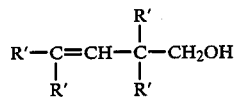

which preferentially cyclize to 2,2,4,4-tetrasubstituted tetrahydrofurans:

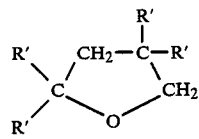

In addition, during the reaction the unsaturated alcohol will undergo dehydration leading to a complex mixture of C-8 dienes and other organic lights. Thus, the avoidance or minimization of the formation of diester, diol, unsaturated alcohol, furan and other by-products in any significant amount is desirably avoided. The process of this invention does so to a high degree since conversions as high as 95% or more to the desired products II and III are achieved. The variables R, R′ and R″ are hereinafter defined.

It was noted that during startup, the inefficiency to undesired by-product might be higher than desired. However, as the reaction proceeded by-product formation was inhibited and significantly reduced, resulting in conversions to desired unsaturated 2,2,4-trisubstituted monoesters at high rates and high yields or selectivity of 90% to 95% or higher.

In the process of this invention the saturated 2,2,4-trisubstituted glycol monoester of the general formula:

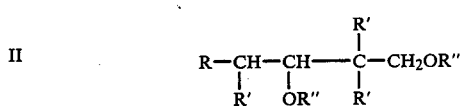   I are catalytically dehydrated at elevated temperature to the unsaturated 2,2,4-trisubstituted monoesters of the formulas:

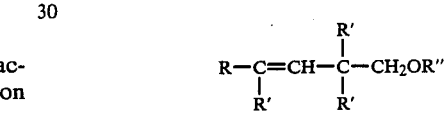

Subgeneric to Formula I are compounds of the formulas:

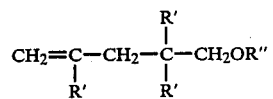   IV and

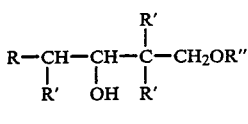   V

In Formulas I to V the R, R′ and R″ groups have the following meanings:

R is hydrogen or an unsubstituted or substituted hydrocarbyl group that can be (i) an alkyl group having from 1 to about 8 carbon atoms, preferably 1 to 4 carbon atoms, (ii) a cycloalkyl group having 5 or 6 ring carbon atoms, or (iii) an aryl, alkaryl or aralkyl group in which the aromatic ring is either phenyl or naphthyl;

R′ is a hydrocarbyl group as defined for R; and

R″ is (i) hydrogen or (ii) an —OCR group with the proviso that in Formula I one of the R′ groups is hydrogen and in Formulas I to V an —OCR′ group is always present.

Compounds of these formulas are well known and many are readily obtainable. The saturated 2,2,4-trisubstituted glycol monoesters are easily synthesized by the process described in U.S. Pat. No. 3,091,632 by the trimeric condensation of the alpha, alpha-disubstituted acetaldehydes. Illustrative of saturated 2,2,4-trisubstituted glycol monoesters are 3-hydroxy-2,2,4-trimethylpentyl isobutyrate, 3-hydroxy-2-ethyl-2,4 dimethylhexyl 2-methylbutyrate, 3-hydroxy 2,2,4-triethylhexyl 2-methylbutyrate, 3-hydroxy 2,2,4-trimethylpentyl acetate, 2-ethyl-3-hydroxy-2,4-dimethylhexyl 2-methylbutyrate, 2-butyl-2,4-diethyl-3 hydroxyoctyl 2-ethylhexanoate, 2,4-diethyl-3-hydroxy-2-isobutylheptyl 2-ethyl-4methylpentanoate, 3-hydroxy-2,2,4-triethylhexyl 2-ethylbutyrate, 2-cyclohexyl-3-hydroxy-2,4-dimethylhexyl 2-cyclohexylpropionate, 3-hydroxy-2,2,4-tricyclohexylbutyl 2,2-dicyclohexylacetate, 2-methyl-3-hydroxy-2,4-di(para-methylphenyl)pentyl 2(para-methylphenyl)propionate, 1-hydroxy-2,2,4-trimethylpentyl-3-isobutyrate, 1-hydroxy-2-ethyl-2,4-dimethylhexyl 3(2-methylbutyrate), 1-hydroxy 2,2,4-triethylhexyl 3(2-methylbutyrate), 1-hydroxy-2,2,4 trimethylpentyl 3-acetate.

The dehydration of the 2,2,4-trisubstituted glycol monoesters of Formulas I, IV and V is readily carried out at elevated temperature in the presence of a catalytic amount of the catalyst sufficient to carry out the dehydration reaction.

The dehydration reaction is carried out in this process at a reaction kettle temperature of from about 170° C. to about 270° C., preferably from about 180° C. to about 250° C. The reaction is preferably carried out in a continuous manner and is compatible with operation in a still with addition of reactants and catalyst to the kettle and continuous removal of unsaturated ester overhead and water of reaction decanted. The column temperature can be controlled by varying the kettle temperature, feed rate, pressure and reflux ratio under which the dehydration reaction is being conducted. The size of the distillation column, the volume of material passing through the column and the temperature of the coolant also affect the column temperature.

The dehydration is catalyzed using a catalytic amount of a substantially non-volatile acid catalyst. Among the suitable catalysts are the weak acids or the strong acids. These are well known to those of ordinary skill in this art and require no further description here. However, in further clarification typical of suitable acids one can mention the alkali metal hydrogen sulfates (e.g., sodium hydrogen sulfate and potassium hydrogen sulfate). p-toluenesulfonic acid (PTSA), sulfuric acid, phosphoric acid, and the like. However, it may be necessary to replenish the catalyst due to carry over with volatile products, in order to maintain a catalytic concentration of the catalyst. It was completely unexpected and unpredictable that dehydration to the desired unsaturated 2,2,4- trisubstituted monoesters of Formulas II and III was achieved in such high yield and rate under the process conditions of this invention in view of the statements in U.S. Pat. No. 3,408,388.

In U.S Pat. No. 3,408,388, the reaction conditions specify a temperature of from 90° C. to 160° C. This reference states that at a dehydration temperature above 160° C., the dehydration of the glycol monoester is nearly complete but in addition to the ester of the unsaturated alcohol, the acid, substituted tetrahydrofurans and other products are formed (column 5, lines 34 to 45). The reference also states that potassium acid sulfate was not effective (column 5, lines 8 to 13). Thus, it was surprising to find that we could produce the unsaturated 2,2,4-trisubstituted monoesters of Formulas II and III in such high yield and rate even by the use of the catalysts sodium hydrogen (acid) sulfate and potassium hydrogen (acid) sulfate. This was completely unexpected and contra to the teachings in the prior art.

The amount of catalyst charged to the reaction kettle is an amount sufficient to catalyze the dehydration reaction. This amount can be from about 0.005 to about 5 weight percent, preferably 0.05 to about 1 weight percent, most preferably from about 0.1 to about 0.5 weight percent based on the amount of saturated 2,2,4-trisubstituted glycol monoester in the reactor. The preferred catalysts are sodium hydrogen sulfate and potassium hydrogen sulfate at concentrations below about 0.5 weight percent.

The reaction is carried out at a pressure of about 100 mm Hg or higher, preferably from about 200 mm Hg to about 750 mm. Pressure is not critical.

It is preferred to maintain as short a contact time as possible in the reactor in order to minimize side reactions. However, this will vary depending upon the size of the reactor and column and the specific reactants and reaction conditions employed.

In general the average contact time of reactants with the non-volatile acid catalysts is from about 0.5 hour or less to about 4.5 hours. Though one can use longer contact periods, it is of no significant advantage and may lead to undesireable reactions.

The reaction is typically carried out in a conventional distillation reactor equipped with a multi-tray distilling column. The reactor is charged with the saturated monoester (e.g. 2,2,4-trisubstituted glycol monoester) and catalyst and heated to the desired temperature at reduced pressure. When the system has reached reflux, make-up saturated monoester is added to the kettle at a feed rate to maintain a constant volume in the reactor and distillates are removed.

The following examples serve to further illustrate the invention.

EXAMPLE 1

To a 2-liter reaction kettle equipped with a 10-tray Oldershaw column and a water cooled automatic reflux head there was added 940 g of an isomeric mixture of 1-hydroxy-2,2,4-trimethylpentyl 3-isobutyrate and 3-hydroxy-2,2,4 trimethylpentyl isobutyrate and 0.94 g (0.1 wt. %) potassium hydrogen sulfate. This isomeric mixture of monohydroxy- 2,2,4-trimethylpentyl isobutyrates is hereinafter referred to as (A). The system was brought to reflux at 150 mm Hg and isomeric monohydroxy-2,2,4-trimethylpentyl isobutyrates (A) was fed to the kettle at the rates shown in Table I.

The column was operated for approximately 10 hours with average feed and make rates of 250–300 cc/hr. Kettle temperature was approximately 180° C., and reflux adjusted to maintain a head temperature of 115° C. The product efficiency to the mixture of the two 2,2,4-trimethylpentenyl-1-isobutyrates (B) isomers was in the 85 to 91% range during this period.

After 10 hours, the kettle was concentrated to half its original level (470 g) to decrease the residence time and increase the acid catalyst concentration. The system was operated under the same conditions for an additional 10 hours and gave comparable results. During the run, between 1.5 and 5.5% monohydroxy-2,2,4 trimethylpentyl isobutyrates (A) was taken overhead with organic lights and 2,2,4-trimethyl-1,3-pentanediol (D).

The 10-tray Oldershaw column was then replaced with a 30-tray Oldershaw column to decrease the amounts of diol (D) and monohydroxy-2,2,4trimethylpentyl isobutyrates (A) taken overhead with the product. The system was restarted and operated for approximately five hour periods under the conditions and with the results in Table 1. A stoichiometric amount of water (~8%) separated from the collected product and was decanted.

TABLE 1

| Reaction Progress (hrs) | Feed Rate (mL/h) | Pressure (mm Hg) | Reflux Ratio | Temp. (°C.) Kettle/Head | Make Rate (mL/h) | Yield % B | % A | % C |
|---|---|---|---|---|---|---|---|---|
| 20–25 | 240 | 145 | 1:4 | 185/104 | 240 | 97.5 | 0 | 0 |
| 26–30 | 245 | 300 | 2:1 | 206/127 | 245 | 96.7 | 0 | 0 |
| 31–35 | 330 | 760 | 2.5:1 | 246/157 | 325 | 95.6 | 0 | 0 |
| Kettle Analysis | | | | | | 31.4 | 38.6 | 26.7 |

C: 2,2,4-trimethylpentyl 1,3-diisobutyrate.
Note:
A portion of this compound is originally present in the charged isomeric mixture (A).

Example 1 clearly demonstrates the high efficiency of the process of this invention at kettle temperatures higher than those previously considered suitable for the reaction and use of potassium hydrogen sulfate as the catalyst, a material previously published as being non-catalytic for this reaction in U.S. Pat. No. 3,408,388.

EXAMPLE 2

This example demonstrates operation of the process of this invention with catalyst levels of 0.01 to 0.05 wt. % The reaction system described in Example 1 (30-tray Oldershaw column) was used to react the isomeric mixture of monohydroxy-2,2,4-trimethyl isobutyrates (A). The system was operated for approximately five hour periods to produce product (B) under the conditions and with the results for each period described in Table 2.

TABLE 2

| Kettle Level (grams) | Feed Rate (mL/h) | Catalyst (wt. %) | Pressure (mm Hg) | Reflux Ratio | Temp (°C.) Kettle/Head | Make Rate (mL/h) | Yield % B | % A | % C |
|---|---|---|---|---|---|---|---|---|---|
| 500 | 95 | KHSO4 (0.01) | 302 | 5:1 | 212/128 | 95 | 96.2 | | |
| 500 | 200 | KHSO4 (0.03) | 302 | 2:1 | 219/120 | 200 | 97.0 | | |
| 670 | 80 | H2SO4 (0.01) | 303 | 1:1 | 221/126 | 60 | 89.4 | | |
| 670 | 245 | H2SO4 (0.05) | 303 | 3:1 | 217/116 | 255 | 96.1 | | |
| Kettle Analysis | | | | | | | 11.8 | 78.6 | 7.0 |

In Example 2 it is shown the process of this invention is consistently effective at the higher temperatures and that considerably lower catalyst concentrations of catalyst can be effectively used.

EXAMPLE 3-a

This example shows operation of the process with p-toluenesulfonic acid monohydrate as the acid catalyst and demonstrates the sensitivity of product composition to the head temperature as controlled by the reflux ratio. The system was operated with the equipment described in Example 2 with an initial charge of 1000 g of monohydroxy-2,2,4-trimethylpentyl isobutyrates (A) using 0.18 wt. % PTSA.H2O. The results of the run are summarized in Table 3. In hours 2–6 the system was operated with a high head temperature which resulted in the codistillation of starting mono-esters (A), with the product (B). Lowering the head temperature during hours 6–12 to 152° C. by increasing the reflux ratio, eliminated the carry over of the monohydroxy-2,2,4-trimethylpentyl isobutyrates (A) starting material.

TABLE 3

| Reaction Progress (hrs) | Pressure (mm Hg) | Feed Rate (mL/h) | Temp (°C.) Kettle/Head | Make Rate (mL/h) | Reflux Ratio | Yield % B | % A | % C | % D |
|---|---|---|---|---|---|---|---|---|---|
| 2–4 | 302 | 590 | 214/155 | 525 | 2:4 | 87.1 | 9.8 | 0 | 0.8 |
| 4–6 | 302 | 495 | 214/165 | 620 | 2:5 | 76.8 | 18.6 | 0 | 0.4 |
| 6–12 | 302 | 400 | 214/152 | 415 | 3:2 | 97.4 | 0 | 0 | 0.7 |
| Kettle Analysis | | | | | | 15.0 | 61.6 | 19.5 | 1.2 |

EXAMPLE 3-b

This example shows operation of the process with the acid catalyst utilized in Example 3-a but at a higher level. The results of the run are summarized in Table 4. The system used for this example consisted of a 40-tray Oldershaw column equipped with a water cooled automatic reflux head and a 500 cc kettle. The system was charged with 233 g of monohydroxy-2,2,4-trimethylpentyl isobutyrates (A) and 0.40 wt. % PTSA.H2O. The results during the first hour demonstrate the inefficiency of the process during startup. During the next four hours, the system stabilizes and the efficiency steadily increases to its normally high yield level for the production of (B).

TABLE 4

| Reaction Progress (hrs) | Pressure (mm Hg) | Feed Rate (mL/h) | Temp (°C.) Kettle/Head | Make Rate (mL/h) | Reflux Ratio | Yield | | | |
|---|---|---|---|---|---|---|---|---|---|
| | | | | | | % B | % A | % C | % D |
| 0–1 | 300 | 65 | 193/70–160 | 55 | 1:10 | 67.3 | 0.9 | 1.4 | 0.1 |
| 1–5 | 302 | 225 | 209/161 | 255 | — | 95.4 | 0.7 | 0.1 | 0.9 |

EXAMPLE 3-c

This example shows the adverse effect of lower pressure on the reaction rate when a weak acid catalyst such as p-toluenesulfonic acid monohydrate is utilized. The system was operated as in Example 2 with an initial charge of 1350 g of monohydroxy-2,2,4-trimethylpentyl isobutyrates (A). The level of acid catalyst (PTSA.H2O) was varied from 0.10 to 0.30 wt. %. During hours 6–25, when the system was operated at 300 torr, a good reaction rate was maintained and high yields of product (B) were achieved with 0.10 wt. % catalyst (see Table 5). When the pressure was decreased to 100 torr, the kettle temperature decreased from 215° C. to 188° C., resulting in in a dramatic decrease in reaction rate at a catalyst concentration of 0.10 wt. % (hours 25–32). Even increasing the acid level three-fold (from 0.10 to 0.30 wt. %; hours 32–39) did not bring the rate back to the level observed when the system was operated at 300 torr. However, desired product (B) was still produced.

TABLE 5

| Reaction Progress (hrs) | Catalyst (wt. %) | Pressure (mm Hg) | Feed Rate (mL/h) | Temp (°C.) Kettle/Head | Make Rate (mL/h) | Reflux Ratio | Yield | | |
|---|---|---|---|---|---|---|---|---|---|
| | | | | | | | % B | % A | % C |
| 6–10 | PTSA (0.10) | 302 | 180 | 213/143 | 190 | 1:2 | 97.2 | | |
| 10–17 | PTSA (0.10) | 302 | 240 | 215/144 | 250 | 2:3 | 95.0 | | |
| Kettle Analysis | | | | | | | 30.0 | 52 | 11.6 |
| 17–25 | PTSA (0.10) | 300 | 250 | 215/145 | 280 | 1:3 | 97.0 | | |
| Kettle Analysis | | | | | | | 16.3 | 62.3 | 17.9 |
| 25–32 | PTSA (0.10) | 100 | 210 | 188/— | 75 | | 57.0 | 39.0 | |
| 32–39 | PTSA (0.30) | 100 | 215 | 188/120–130 | 195 | 2:4 | 92.3 | 4.6 | |

EXAMPLE 4

This example demonstrates operation of the process with sodium hydrogen sulfate (NaHSO4) as the acid catalyst at various pressures. The system was operated with the equipment described in Example 2 with an initial charge of 1000 g of monohydroxy-2,2,4-trimethylpentyl isobutyrates (A) and using 0.10 wt. % NaHSO4. With the exception of startup (1–3 hours), the reaction is highly efficient (95+%) at all the pressures examined (see Table 6). Even at atmospheric pressure (30–36 hours), the reaction proceeds with a high efficiency and rate to product (B).

TABLE 6

| Reaction Progress (hrs) | Pressure (mm Hg) | Feed Rate (mL/h) | Temp (°C.) Kettle/Head | Make Rate (mL/h) | Reflux Ratio | Yield | | | |
|---|---|---|---|---|---|---|---|---|---|
| | | | | | | % B | % A | % C | % D |
| 1–3 | 301 | 180 | 192/145 | 240 | 1:1 | 82.9 | | | |
| 4–11 | 300 | 255 | 197/146 | 245 | 2:4 | 97.0 | 0 | 0 | 0.3 |
| Kettle Analysis | | | | | | 46 | 37 | 13 | |
| 12–20 | 150 | 255 | 188/129 | 330 | 2:4 | 96.7 | 0 | 0 | 0.4 |
| Kettle Analysis | | | | | | 23.6 | 44.8 | 24.6 | |
| 21–29 | 302 | 325 | 207/148 | 387 | 2:3 | 96.7 | 0 | 0 | 0.4 |
| Kettle Analysis | | | | | | 26.4 | 40.7 | 25.9 | |
| 30–36 | 760 | 575 | 253/177 | 476 | 1:1 | 95.6 | 0 | 0 | 0.3 |
| Kettle Analysis | | | | | | 16.0 | 48 | 28 | |

EXAMPLE 5

This example demonstrates operation of the process with the catalyst (NaHSO4) over a longer period of time. The system used for this example consisted of a 40-tray Oldershaw column equipped with a water cooled automatic reflux head and a 2-liter kettle. The kettle was charged with 1500 g of monohydroxy-2,2,4-trimethylpentyl isobutyrates (A) and 0.20 wt. % NaHSO4. The run was performed over a 70 hour period using a total feed of 26.2 liters. The column was operated at 300 torr, and the reaction rate and efficiency to product (B) were high (see Table 7) throughout the run. Kettle analyses taken at various intervals showed that the 2,2,4-trimethylpentyl 1,3-disobutyrate content of the kettle gradually increased throughout the run (from 7.2 to 50.8%) with no observable adverse effect on the dehydration reaction. It is to be noted that diester is initally present in trace amount in feed (A) and is also formed during the reaction by the process of this invention.

TABLE 7

| Reaction Progress (hrs) | Feed Rate (mL/h) | Total Feed (mL) | Pressure (mm Hg) | Reflux Ratio | Temp (°C.) Kettle/Head | Make Rate (mL/h) | Yield % B | % D | % A | % C |
| --- | --- | --- | --- | --- | --- | --- | --- | --- | --- | --- |
| 2–4 | 518 | 1485 | 305 | 3.5:1 | 178/160 | 551 | 95.3 | 0.40 | | |
| Kettle Analysis | | | | | | | 50.8 | 1.31 | 36.3 | 7.2 |
| 6–8 | 615 | 3990 | 309 | 4:3 | 182/156 | 645 | 94.0 | 0.41 | | |
| 9–11 | 458 | | 303 | 5:3 | 184/157 | 500 | 94.1 | 0.44 | | |
| 11–13 | 380 | 6420 | 302 | 4:3 | 184/156 | 482 | 94.1 | 0.37 | | |
| 16–18 | 330 | 7975 | 300 | 3:4 | 185/158 | 402 | 95.0 | 0.28 | | |
| 19–21 | 327 | | 302 | 3:5 | 193/158 | 395 | 95.6 | 0.18 | | |
| 22–24 | 327 | 10215 | 302 | 3:5 | 195/158 | 402 | 96.0 | 0.33 | | |
| Kettle Analysis | | | | | | | 38.9 | 0.39 | 28.1 | 27.4 |
| 27–29 | 325 | | 302 | 3:5 | 197/158 | 428 | 96.6 | 0.38 | | |
| 29–31 | 327 | 12310 | 303 | 3:5 | 199/158 | 383 | 96.8 | 0.20 | | |
| Kettle Analysis | | | | | | | 32.2 | 0.31 | 31.6 | 30.8 |
| 33–34 | 320 | | 300 | 3:5 | 197/157 | 328 | 96.1 | 0.17 | | |
| 35–36 | 330 | 14410 | 300 | 3:5 | 198/157 | 353 | 97.0 | 0.19 | | |
| 38–40 | 325 | | 302 | 3:5 | 198/159 | 352 | 97.1 | 0.26 | | |
| 40–42 | 288 | 16430 | 302 | 3:6 | 200/157 | 355 | 96.9 | 0.24 | | |
| Kettle Analysis | | | | | | | 28.8 | 0.30 | 29.1 | 36.3 |
| 43–45 | 280 | | 300 | 3:5 | 201/157 | 325 | 96.2 | 0.35 | | |
| 46–48 | 285 | 18200 | 303 | 3:5 | 204/158 | 295 | 97.7 | 0.20 | | |
| 49–51 | 310 | | 302 | 3:5 | 204/157 | 440 | 97.5 | 0.22 | | |
| 51–53 | 385 | 20460 | 302 | 3:3 | 205/154 | 275 | 96.5 | 0.19 | | |
| Kettle Analysis | | | | | | | 26.7 | | 25.7 | 41.2 |
| 54–56 | 403 | | 300 | 3:7 | 197/156 | 480 | 94.7 | 0.35 | | |
| 57–59 | 316 | 22762 | 300 | 3:5 | 200/156 | 436 | 95.9 | 0.22 | | |
| Kettle Analysis | | | | | | | 26.8 | | 15.0 | 50.8 |
| 61–63 | 368 | 24442 | 300 | 3:5 | 202/154 | 460 | 95.0 | 0.34 | | |
| Kettle Analysis | | | | | | | 26.9 | | 14.9 | 50.4 |
| 65–67 | 350 | 26202 | 300 | 3:10 | 202/156 | 433 | 96.2 | 0.43 | | |
| 68–70 | 0 | | 300 | 7:3 | 219/166 | 300 | 96.9 | 0.16 | | |

EXAMPLE 6

This example demonstrates operation of the process for the preparation of high purity product that is free of water and organic lights. Furthermore, the system was shown to run well using a crude feed that consisted of 93% isomeric monohydroxy-2,2,4-trimethylpentyl isobutyrates (A), 2.5% of 2,2,4-trimethyl-1,3 pentanediol and 2.6% 2,2,4-trimethylpentyl 1,3-diisobutyrate. The diol and diisobutyrate were added to determine whether they would have any significant effect on the catalytic reaction. The system used for this example consisted of a 2-liter kettle, 30-tray and 20-tray Oldershaw columns that were connected via a liquid takeoff adapter, and a water cooled automatic reflux head.

The crude feed was fed to the 2-liter kettle (initial charge of 1350 g) and a mid-column make (composed mostly of product (B)) was taken 30 trays above the kettle, while organic lights and water were taken overhead (50 trays above the kettle). The column was operated at 300 torr using 0.30 wt. % sodium hydrogen sulfate as the acid catalyst. The composition of the mid-column make (98+% product (B)) was excellent as shown in Table 8. The overhead make rate was low when compared to the mid-column make rate.

TABLE 8

| Reaction Progress (hrs) | Feed Rate (mL/h) | Temp. (°C.) Kettle/ Mid-Column/ Head | Mid-Column Make Rate (mL/h) | Overhead Make Rate (mL/h) Organic/Water | Composition of Mid-Column Make % B | % D | % A | % C |
| --- | --- | --- | --- | --- | --- | --- | --- | --- |
| 3–5 | 327 | 199/168/120 | — | — | 98.8 | 0.68 | 0 | 0 |
| 8–12 | 221 | 200/169/100 | — | — | 99.1 | 0.37 | 0 | 0 |
| Kettle Analysis | — | — | — | — | 44.6 | 0.86 | 18.0 | 29.4 |
| 12–15 | 425 | 202/169/97 | 371 | 40[1]/34 | 98.6 | 0.65 | 0 | 0 |
| 15–20 | 398 | 212/168/96 | 348 | 45[2]/33 | 97.7 | 1.5 | 0 | 0 |
| Kettle Analysis | — | — | — | — | 13.6 | 0.42 | 39.3 | 40.4 |
| 21–24 | 368 | 213/168/85 | 340 | 28[3]/30 | 98.6 | 0.80 | 0 | 0 |

[1] 58% B, 42% Lights
[2] 52% B, 47% Lights
[3] 32% B, 68% Lights

EXAMPLE 7

This example shows operation of the process in the batch mode. The system used for this example consisted of a 40-tray Oldershaw column equipped with a water cooled automatic reflux head and a 3-liter kettle. The system was charged with 2 kg of monohydroxy-2,2,4-trimethylpentyl isobutyrates (A) and 0.30 wt. % NaH- SO4. The results from the batch reaction are summarized in Table 9. With the exception of startup (0–2 hours), the reaction is highly efficient (>90%). Near the end of the reaction (14–16 hours), product B distilled overhead in high purity (99%).

TABLE 9

| Reaction Progress (hrs) | Pressure (mm Hg) | Temp. (°C.) Kettle/Head | Reflux Ratio | Yield % B |
|---|---|---|---|---|
| 0–2 | 300 | 180/90 | 2:1 | 7.5 |
| 3–5 | 300 | 180/152 | 2:1 | 95.9 |
| 6–10 | 300 | 183/154 | 3:1 | 90.6 |
| 10–13 | 300 | 184/162 | 4:1 | 93.6 |
| 14–16 | 300 | 198/172 | 1:2 | 99.1 |

EXAMPLE 8

This example demonstrates operation of the process of this invention using a crude mixed feed of 2-ethyl-2,4-dimethyl-3-hydroxy-hexyl-1-(2-methyl butyrate) and 2-ethyl-2,4 dimethyl-1 hydroxy hexyl 3(2 methyl butyrate) (E). This feed also contained several percent 2-ethyl-2,4-dimethyl-1,3-hexanediol (F) and 2-ethyl-2,4-dimethyl-1,3-hexanediol di(2-methyl butyrate) (G). An initial charge of 1482 g of the monohydroxy 2-ethyl-2,4-dimethyl hexyl (2-methyl butyrates) (E) was used together with 3.2 g (0.21%) sodium hydrogen sulfate catalyst in the reaction system described in Example 1 (30-tray Oldershaw column). The reaction system was operated for 34 hours with typical results described in Table 10. In addition to the expected mixture of 2-ethyl-2,4-dimethylhexenyl 1-(2 methyl butyrates) (H) some of the isomeric 2-ethyl-2,4-dimethyl-hexen-1-ols (I) codistilled with the product (H). With this feed, yields to desired product (H) were lower than in Examples 1 to 7, but applicants are still able to produce product (H) at the conditions of temperature and catalyst heretofore considered not applicable in U.S. Pat. No. 3,408,388.

TABLE 10

| Reaction Progress (hrs) | Pressure (mm Hg) | Feed Rate ml/hr. | Temp. (°C.) Kettle/Head | Make Rate (ml/hr.) | Reflux Ratio | Yield % H | % F | % I |
|---|---|---|---|---|---|---|---|---|
| 7–8 | 152 | 480 | 236/186 | 260 | 1/10 | 87.3 | 4.9 | 5.2 |
| 11–12 | 100 | 280 | 227/169 | 140 | 4/2 | 68.5 | 16.5 | 8.6 |
| 28–29 | 100 | 80 | 196/170 | 70 | 10/2 | 75.4 | 7.7 | 6.8 |

What is claimed is:

1. A process for the production of unsaturated 2,2,4-trisubstituted monoesters of the formulas:

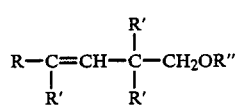  II and

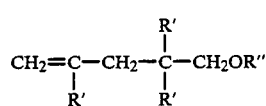  III by the catalytic dehydration of a saturated 2,2,4-trisubstituted glycol monoester of the formula:

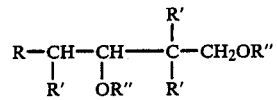  I in contact with a catalytic amount of a substantially non-volatile acid catalyst sufficient to catalyze the dehydration reaction at a temperature of from about 170° C. to about 270° C., said catalyst being selected from the group consisting of sodium hydrogen sulfate and potassium hydrogen sulfate, wherein:

R is hydrogen or an R' group;

R' is (i) an alkyl group having from 1 to about 8 carbon atoms, (ii) a cycloalkyl group having 5 or 6 ring carbon atoms, or (iii) an aryl, or aralkyl group in which the aromatic ring is phenyl or naphthyl; and R" is (i) hydrogen or (ii) an —OCR' group with the proviso that in Formula I one of the R" groups is hydrogen and in Formulas I, II and III and —OCR' group is always present.

2. A process as claimed in claim 1 wherein Compound (I) has the formula:

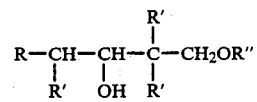  IV and R" is an —OCR' group.

3. A process as claimed in claim 1 wherein Compound (I) has the formula:

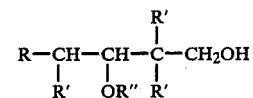  V and R" is an —OCR' group.

4. A process as claimed in claim 1 wherein R' is an alkyl group having from 1 to about 4 carbon atoms.

5. A process as claimed in claim 1 wherein R and R' are methyl.

6. A process as claimed in claim 1 wherein the unsaturated 2,2,4-trisubstituted monoesters is a mixture of the ethyldimethylhexylene 2-methyl butyrate isomers.

7. A process as claimed in claim 1 wherein the dehydration reaction is carried out at a temperature of from about 180° C. to about 250° C.

8. A process as claimed in claim 1 wherein the acid catalyst is sodium hydrogen sulfate.

9. A process as claimed in claim 1 wherein the acid catalyst is potassium hydrogen sulfate.

10. A process as claimed in claim 1 wherein Compound (I) is 3-hydroxy-2,2,4-trimethylpentyl isobutyrate.

11. A process as claimed in claim 1 wherein said unsaturated 2,2,4-trisubstituted monoester is a mixture of the unsaturated isomers of 2,2,4-trimethylpentenyl-1-isobutyrate.

12. A process as claimed in claim 1 wherein the saturated 2,2,4-trisubstituted glycol monoester is 3-hydroxy-2,2,4-trimethylpentyl isbutyrate and the unsaturated 2,2,4-trisubstituted monoester is a mixture of 2,2,4-trimethyl-3-pentenyl isobutyrate and 2,2,4-trimethyl-4-pentenyl isobutyrate.

13. A process as claimed in claim 1 wherein the saturated 2,2,4-trisubstituted glycol monoester is 3-hydroxy-2,2,4-trimethylpentyl isbutyrate and the unsaturated 2,2,4-trisubstituted monoester is a mixture of 2,2,4-trimethyl-3-pentenyl isobutyrate and 2,2,4-trimethyl-4-pentenyl isobutryate, the acid catalyst is sodium hydrogen sulfate and the temperature is from about 180° C. to about 250° C.

14. A process as claimed in claim 1 wherein the saturated 2,2,4-trisubstituted glycol monoester is 3-hydroxy-2,2,4-trimethylpentyl isobutyrate and the unsaturated 2,2,4-trisubstituted monoester is a mixture of 2,2,4-trimethyl-3-pentenyl isobutyrate and 2,2,4-trimethyl-4-pentenyl isobutyrate, the acid catalyst is potassium hydrogen sulfate and the temperature is from about 180° C. to about 250° C.

* * * * *